United States Patent [19]

Weismuller

[11] Patent Number: 4,771,173

[45] Date of Patent: Sep. 13, 1988

[54] CONTACTLESS APPARATUS AND METHOD FOR THICKNESS DETERMINATION OF COATINGS

[75] Inventor: Thomas P. Weismuller, Orange, Calif.

[73] Assignee: Rockwell International Corporation, El Segundo, Calif.

[21] Appl. No.: 882,754

[22] Filed: Jul. 7, 1986

[51] Int. Cl.$^4$ .......................................... G01N 23/203
[52] U.S. Cl. ................................. 250/308; 250/358.1
[58] Field of Search ............... 250/308, 358.1, 359.1, 250/360.1; 378/89; 350/507, 518, 532, 521, 530

[56] References Cited

U.S. PATENT DOCUMENTS

| | | | |
|---|---|---|---|
| 2,855,518 | 10/1958 | Foley et al. | 250/308 |
| 2,951,159 | 8/1960 | Mariner | 250/308 |
| 3,019,336 | 1/1962 | Johns | 250/308 |
| 3,259,012 | 7/1966 | Locquin | 350/521 |
| 3,364,354 | 1/1968 | Fries | 250/308 |
| 3,620,595 | 11/1971 | Loop et al. | 350/530 |
| 3,720,833 | 3/1973 | Hay | 250/308 |
| 3,860,820 | 1/1975 | Ryan | 250/360.1 |
| 4,155,009 | 5/1979 | Lieber et al. | 250/308 |
| 4,406,948 | 9/1983 | Fischer et al. | 250/308 |
| 4,424,445 | 1/1984 | Joffe et al. | 250/308 |
| 4,437,012 | 3/1984 | Cavy et al. | 250/308 |
| 4,441,022 | 4/1984 | Joffe et al. | 250/308 |
| 4,449,048 | 5/1984 | Pinches et al. | 250/308 |
| 4,451,732 | 5/1984 | Spongr et al. | 250/308 |
| 4,531,816 | 7/1985 | Baumgärtel | 350/507 |

OTHER PUBLICATIONS

Transmittance and Reflectance of a Coated Substrate with Application to Index Measurement of Thin Films J. Appl. Phys., vol. 49, 2/2/78, pp. 801–803, J. SooHoo et al.

Analyzing Semiconductors with Auger Spectrocopy Test & Measurement World, 9/83, pp. 76–82, S. I. Ingrey.

*Primary Examiner*—Janice A. Howell
*Assistant Examiner*—William F. Rauchholz
*Attorney, Agent, or Firm*—H. Fredrick Hamann; George A. Montanye; Jonathan B. Orlick

[57] ABSTRACT

An apparatus and method for measuring the thickness of thin basal coatings on work pieces. The apparatus comprises a beta backscatter type measuring instrument including a work piece positioning system to permit the precise positioning of a coated work piece surface to radiation in a repeatable, non-destructive, non-contacting position with respect to the radiation source.

17 Claims, 4 Drawing Sheets

CONTACTLESS APPARATUS AND METHOD FOR THICKNESS DETERMINATION OF COATINGS

BACKGROUND OF THE INVENTION

1. Field of the Invention

This invention relates generally to coating thickness measuring devices, and more particularly to an instrument and method for the non-destructive contactless measurement of contact sensitive, thin coatings on basal substrates by beta-ray backscatter techniques and, even more specifically, to an improved optical system for beta-ray measuring instruments for precisely locating the beta-ray source in a non-contacting position with respect to the specimen to be measured.

2. Description of the Prior Art

Beta-ray backscatter measuring instruments have been extensively utilized to measure the thickness of metallic deposits and coatings of various materials such as, for example, the conductive plating on printed circuit boards or the like. These instruments generally include a source of beta radiation, conveniently a radioactive isotope. This source emits radiation whicn is directed to strike a metallic coating and the radiation backscatter from the coating is measured by a detector in the form of a Geiger-Mueller tube. An associated electronic counter or readout unit converts the output of the detector into utilizable intelligence.

The accuracy and sensitivity of the beta-ray backscatter instrument is largely dependent upon the geometry of the system, that is, the geometric or positional relationship between the source, work piece and detector, and to this end auxiliary means for locating the work piece relative to the source and detector are usually incorporated, in accordance with the dictates of the work piece configuration, as a component of most such measuring systems.

These type of instruments are highly useful in taking measurements of thin coatings on basal substrates, however, problems have arisen, compounded by the continued drive towards miniaturization, in properly locating and precisely controlling the area of the specimen to be exposed to radiation, as well as in maximizing the areas to be exposed to radiation when the radiation source is necessarily disposed remote therefrom to permit specimen positioning.

Another problem with present beta-ray backscatter techniques is, that heretofore, a contact method has been used. More specifically, the sample is placed in intimate contact with the metallic surface over which it is then scanned by the Geiger-Mueller detector. This generally is not as much of a problem in the plating industry where this method is used because the metallic surfaces have a much higher forgiveness for being contacted with other metal surfaces. However, in certain cases, contact of any type is detrimental when the surface to be measured is very soft and brittle. For example, thickness measurements requiring direct physical contact with epitaxial coatings of mercury cadmium telluride (HgCdTe) or of cadmium telluride (CdTe) electro optical films result in the destruction or damage of the coating.

There are several methods that have been used and are being used to determine the thickness of epitaxial deposits. In the case of HgCdTe or CdTe, one method has been to use destructive cleave measurements. This method basically contemplates the taking of the deposited substrate sample and breaking it up by cleaving it along a fracture line, and then microscopically examining a cross-section of that piece to visually determine the thickness of the epitaxial coating. This method has the obvious disadvantage of being destructive and, therefore, would not be suitable for a production line type determination.

Another method of determining the thickness of epitaxially deposited coatings which is non-destructive is by measuring optical interference fringes. This is accomplished with the use of an infrared spectrometer by performing an optical transmission in the desired infrared region. Results from such a transmission are sine-shaped interference fringe patterns. The period of these fringes, in other words, the distance between the peak to the peak of the sine waves plotted by the infrared spectrometer, is calculatable back to what the thickness of the epitaxial deposit is. This particular method is commonly utilized and is compatible with production line environments and is well known in the art. (For example, see an article entitled "Transmittance and Reflectance of a Coated Substrate with Application to Index Measurement of Thin Films", by J. SooHoo and R. D. Henry, J. Appl. Phys., Vol. 49, No. 2, February 1978.) One disadvantage of this method, however, is that the instrument itself is very expensive. The process is time consuming, taking several minutes for each determination, as well as for each standardization procedure which must be performed periodically. More specifically, the sample to be measured must be placed in a chamber and purged of air so there is additional waiting time incurred before a measurement can even be taken. A measurement using the infrared spectrometer typically runs approximately three minutes followed by an additional three minute purge process. Another major disadvantage to the use of the infrared spectrometer is that not only is it time consuming but also that it is not adequate for use with samples where the coating or the substrate has uneven or irregular surfaces. An irregular surface results in an interference pattern which is not readily interpretable.

Another approach to thickness determination which is destructive to the sample, is scanning electron microscope (SEM), auger, or similar instrumental analysis. These analyses require samples to be sectioned into small pieces and then subjected to time consuming and destructive measurement. This particular method is acceptable for production spot analysis but is certainly unsuitable for in-line production thickness measurements. An article of interest in this area appeared in Test and Measurement World, pgs. 76-82, September 1983, entitled "Analyzing Semiconductors with Auger Spectroscopy."

From the foregoing, the need should be appreciated for a production line, non-destructive, contactless, measurement apparatus and method for determining the thickness of thin coatings on contact sensitive basal substrates by beta-ray backscatter techniques. Accordingly, a fuller understanding of the invention may be obtained by referring to the Summary of the Invention, and the Detailed Description of the Preferred Embodiment, in addition to the scope of the invention defined by the claims taken in conjunction with the accompanying drawings.

SUMMARY OF THE INVENTION

The invention is defined by the appended claims with a specific embodiment shown in the attached drawings.

For the purpose of summarizing the invention, the one embodiment comprises a coating measuring system which includes a means for accurately and repeatedly positioning a work piece for the measurement of coating thicknesses. A radiation source is carried by the device, and a radiation detector is provided to measure the amount of backscatter, which is correlated to the thickness of the coating being measured. The radiation source and the radiation detector are carried in a measuring objective which includes an aperture which is brought into a close but non-contacting position with respect to the area of the coating thickness to be measured. More particularly, the distance between the measuring objective and the work piece is accurately and repeatedly controlled via the use of an optical focusing system.

It is an object of this invention to provide an apparatus which overcomes the aforementioned inadequacies of the prior art devices and provides an improvement which is a significant contribution to the advancement of coating thickness measuring device art.

Another object of this invention is to provide a system that yields uniform, accurate thickness measurements on coatings that have uneven or irregular surfaces.

It is yet another object of this invention to provide a system for non-destructive thickness determination of contact sensitive epitaxially deposited films.

Another object of this invention is to provide a portable device for measuring coating thickness incorporating a radioactive isotope source and a detector.

Still another object of this invention is the provision of an optical system for providing a visual indicator on a work piece surface of the exact area to be subjected to beta-ray exposure preparatory to moving a remotely located radiation source into a close but non-contacting position therewith.

It is a further object of the present invention to provide a fast, accurate and cost effective thickness measuring apparatus utilizable in a production line environment.

The foregoing has summarized the invention and has outlined some of the more pertinent objects of the invention. The objects should be construed to be merely illustrative of some of the more prominent features and applications of the intended invention. Many other beneficial results can be obtained by applying the disclosed invention in a different manner or modifying the invention within the scope of the disclosure. The summary has outlined rather broadly the more pertinent and important features of the present invention in order that the detailed description of the invention that follows may be better understood so that the present contribution to the art can be more fully appreciated.

Additional features of the invention will be described hereinafter which will form the subject of the claims of the invention. It should be appreciated by those skilled in the art that the conception and the specific embodiment disclosed may be readily utilized as a basis for modifying or developing other structures and methods for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

Further objects and advantages of the present invention will become apparent as the following description of the preferred embodiment proceeds, taken in conjunction with the accompanying drawings in which.

Similar reference characters refer to similar parts throughout several views of the drawings.

Figure 1:
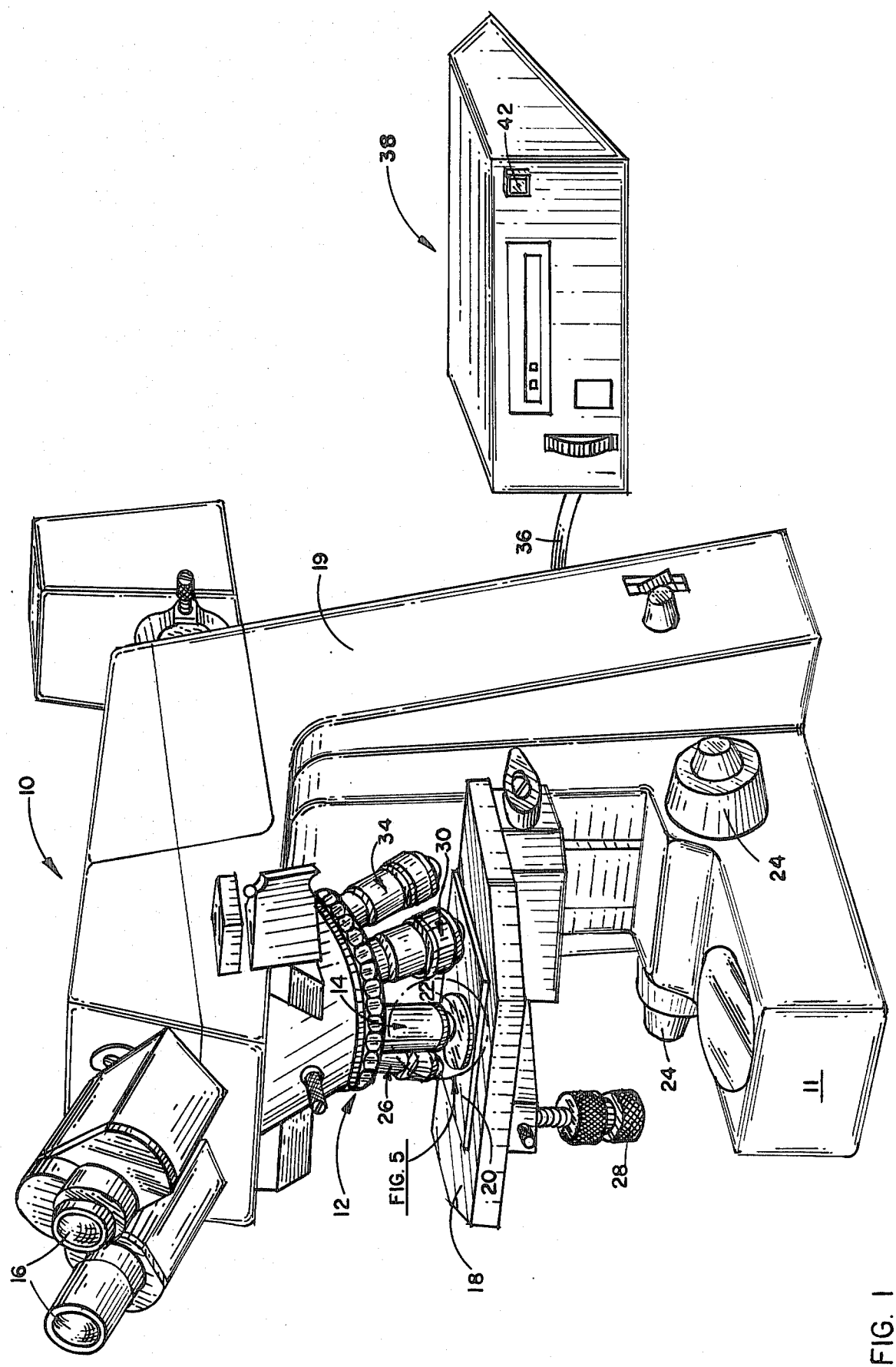
FIG. 1 is a perspective view of the invention illustrating the optical system and an electronic readout unit.

Drawing reference numbers:
10. thickness determination apparatus
11. base of 10
12. turret assembly
14. visual objective
16. eye pieces
18. X-Y positioning fixture
19. support housing
20. non-contaminating surface
22. coated work piece
24. focusing knobs
26. thickness measuring (cadmium 109) detector
28. X-Y stage control
30. thickness measuring (promethium 147) detector
34. thickness measuring (strontium 90) detector
36. detector input/output cable
38. electronic readout counter unit
42. start button
44. threaded base
48. isotope pedestal
50. screw for 48
52. Geiger-Mueller detector tube
54. set screw for 52
56. cable exit orifice
57. threads
58. upper casing
59. lower casing
60. exposure aperture in 30
61. interface between 58 and 59
62. visual objective body length
64. measuring detector body length
66. working distance of visual objective

DESCRIPTION OF THE PREFERRED EMBODIMENT

Figure 2:
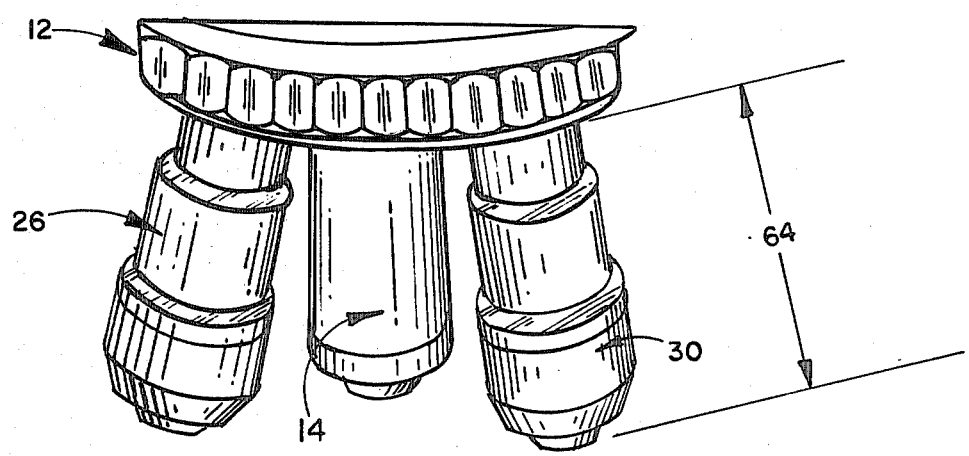
FIG. 2 is an enlarged side elevational view of the optical system turret area and of two thickness measuring detectors.

Referring now to the drawings, and particularly to FIGS. 1 and 2 thereof, there is shown a thickness determination apparatus 10 according to the present invention and which includes a base 11 on which the several elements of the device are positioned and supported. A coated work piece 22, the coating thickness of which is to be measured is shown resting upon a non-contaminating surface 20 of an X-Y positioning fixture 18. The X-Y positioning fixture 18 is in turn adjustably supported via a support housing 19. A turret assembly 12 which is also supported via support housing 19, comprises a visual objective 14, a (cadmium 109) thickness measuring detector 26, a (promethium 147) thickness measuring detector 30, and a (strontium 90) thickness measuring detector 34.

A rotatable turret assembly 12 is provided for the placement of different measuring detectors and objectives over the coated work piece 22. The eye pieces 16 are supported by the support housing 19 and are in an optical communication with the visual objective 14. The principles and physical arrangements of this optical communication functions in accordance with the ordinary laws of reflection and refraction, common to that of ordinary laboratory microscopes. Without departing from the spirit and scope of the invention, it is noted that the preferred embodiment of the turret assembly 12 as illustrated in the drawings and described herein, is only one particular embodiment which may be utilized in conjunction with the invention. Accordingly, the number and type of detectors, visual objectives and the means for their movement over the coated work piece 22 may vary. For example, a sliding horizontal bar engaged with the support housing 19 having detectors and objectives attached thereto, is contemplated by the present invention.

An adjustment X-Y stage control 28 is provided for the horizontal movement of the X-Y stage 18. Focusing knobs 24 act to position the X-Y stage 18 in a vertical position with respect to the visual objective 14. Proper adjustment of the focusing knobs 24 will bring the coated work piece 22 into focus. The X-Y stage control 28 in conjunction with the X-Y positioning fixture 18 permits any selected area of the coated work piece 22 to be subjected to beta radiation. This is useful when the thickness of several portions of the surface of the coated work piece 22 are to be measured. The structure contemplated by the X-Y stage control 28 and the focusing knobs 24 is commonly used with microscopes and is well known by those skilled in the art.

Figure 3:
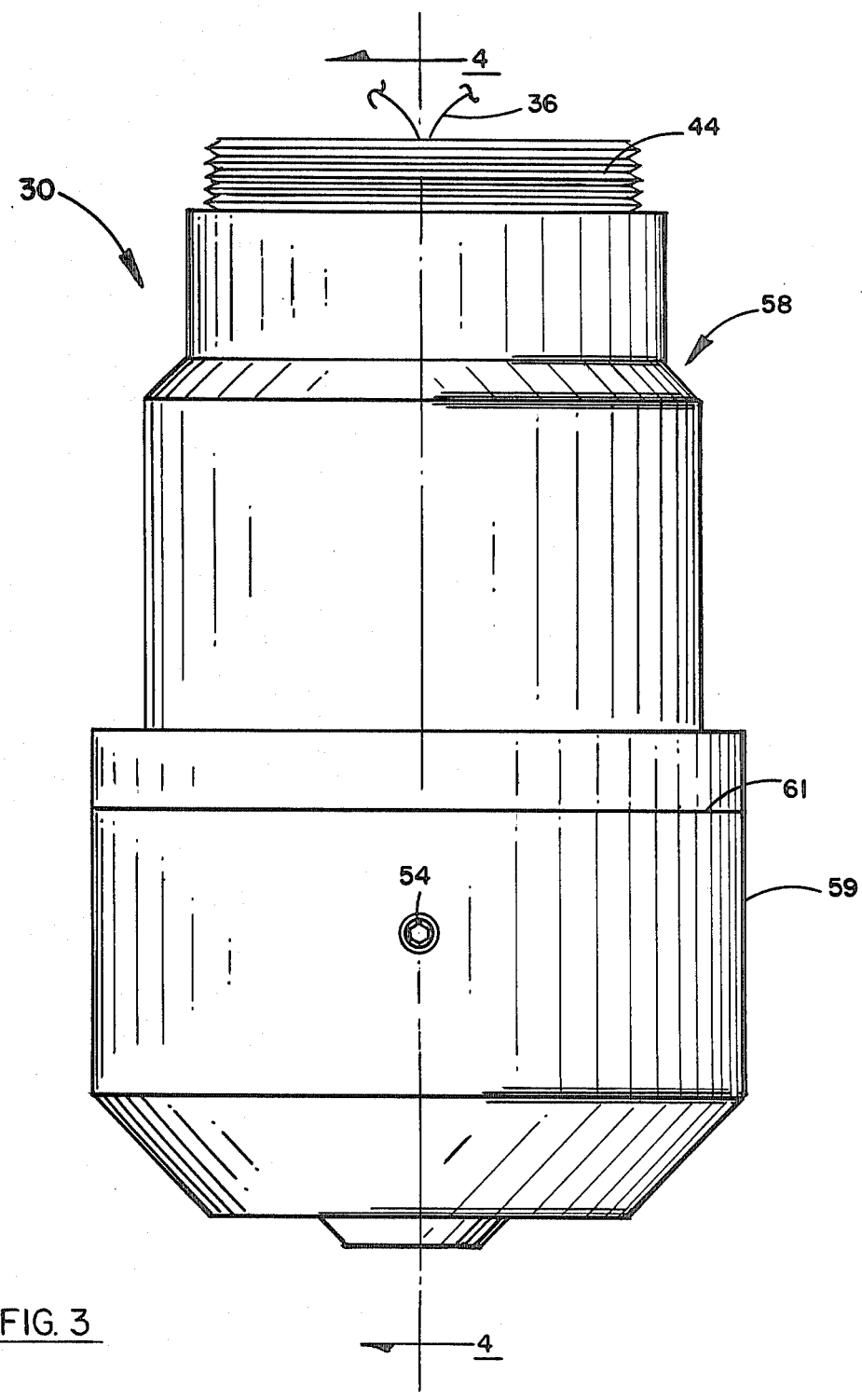
FIG. 3 is an enlarged front elevational view of the thickness measuring detector 30.

Referring now to FIG. 3, an enlarged perspective view of a representative thickness measuring detector 30 is illustrated. More specifically, the thickness measuring detector 30 comprises an upper casing 58, a lower casing 59, a set screw 54 which maintains a Geiger-Mueller detector tube 52 that is incorporated within the lower casing 59, shown in FIG. 4, and a threaded base 44.

The threaded objective base 44 is provided for interconnection with matching threaded grooves (not shown) in the turret assembly 12. It should be appreciated that the representation shown in FIGS. 3 and 4 of the threaded base 44 is merely illustrative of one possible means for attaching thickness measuring detector 30 to the turret assembly 12, and should not be construed as limiting the subject invention to the specific diagrammatic representation as shown and described.

A cable exit orifice 56 (56 shown in FIG. 4) is provided to allow passage of the detector input/output cable 36 from upper casing 58 through the turret assembly 12 into the positioning fixture support arm 19 and finally out through support housing 19 to a conventional electronic readout counter unit 38 (38 shown in FIG. 1). A suitable readout unit is obtainable from Twin City International, Inc., 175 Pineview Drive Audubon Industrial Park, Amherst, N.Y. 14150.

Figure 4:
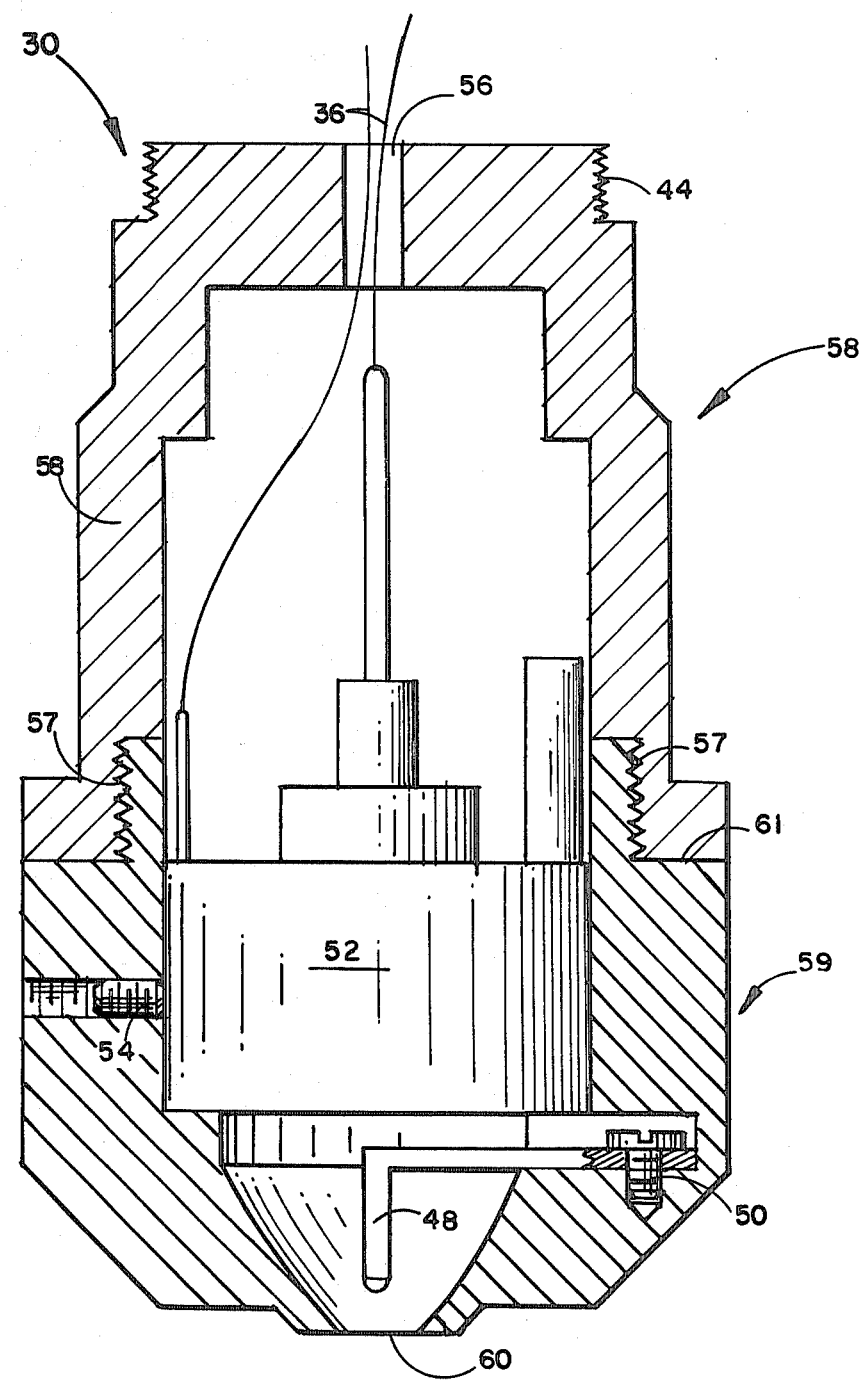
FIG. 4 is a cross-sectional view taken along line 4—4 of FIG. 3.

Turning now to FIG. 4, a cross-sectional view has been taken along line 4—4 of FIG. 3 illustrating a representative thickness measuring detector 30. In this view, a lower casing 59 is shown screwed into an upper casing 58 forming an interface 61 therebetween. This bicameral construction allows for ease of manufacture and for access to repair the inner components of the thickness measuring detector 30.

The thickness measuring detector 30 further comprises an isotope pedestal 48 which is shown securely attached to the casing 59 via screw 50. The isotope pedestal 48 is essentially a holder for one of any number of desired radio-active isotopes. In this specific example, the isotope held by pedestal 48 is promethium 147. The isotope pedestal in thickness measuring detector 34 contains strontium 90 and the isotope pedestal in the thickness measuring detector 26 contains cadmium 109 via threads 57 (measuring detectors 34 and 26 are each respectively shown in FIG. 1).

Input/output cables 36 are shown in FIGS. 3 and 4 exiting through a cable exit orifice 56. An exposure aperture 60 is provided so that the beta radiation which is rather non-penetrating in nature can pass from thickness measuring detector 30 to strike the desired portion on the surface of the coated work piece 22 (22 shown in FIGS. 1 and 5). The Geiger-Mueller tube 52 is shown firmly affixed within the lower casing 59 by set screw 54. The system contemplated by the isotope pedestal 48 and the Geiger-Mueller tube 52 may be of any suitable type and for illustrative purposes is suitably of the general type and character as disclosed in U.S. Pat. No. 3,720,833.

Figure 5:
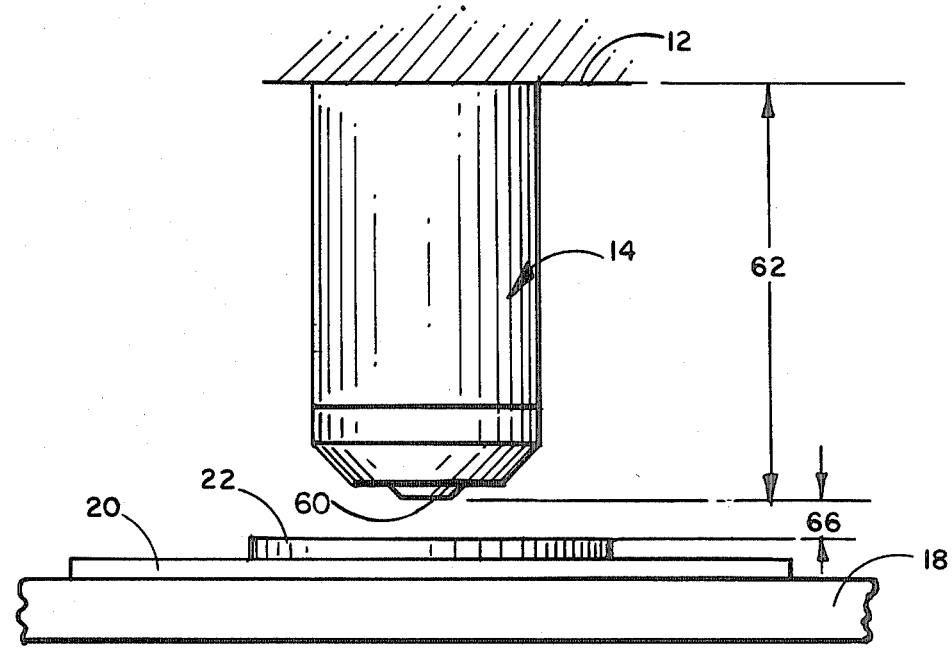
FIG. 5 is an enlarged elevational view of the area indicated in phantom lines on FIG. 1.

FIG. 5 is an enlarged elevational view of the area indicated in phantom lines of FIG. 1. It is essential that a geometry is provided which will allow a working distance to exist between the coated work piece 22 and the exposure aperture 60 such that suitable calibration curves can be generated, with adequate measurement precision, so as to be displayed in a meaningful fashion on a conventional electronic readout unit 38 (38 shown in FIG. 1). More particularly, the working distance 66 between the coated work piece 22 and the exposure aperture 60 must be kept constant to within $+/-3$ microns to maintain repeatability and accuracy of thickness measurements from coated work piece to coated work piece. If the working distance 66 is much greater than 5 millimeters from the coated work piece 22, then the Geiger-Mueller tube 52 (52 shown in FIG. 4) will be unable to detect the radioactive backscatter due to a low signal to noise ratio.

Accordingly, this working distance 66, repeatable to $+/-3$ microns, is achieved by obtaining an optical focus on the surface of the coated work piece 22 and then by moving the desired thickness measuring detector of a predetermined length into place over the coated work piece 22 via turret assembly 12. More specifically, this structural relationship, as illustrated in FIGS. 2 and 5, is governed by the following example equation:

Working distance over coated work piece =

(visual objective 14 body length 62 − thickness measuring detector 30 body length 64) + working distance 66 of visual objective 14.

Typically, a standard visual objective with a working distance of 2.4 millimeters is chosen, which requires the measuring detector body length to be slightly longer than the visual objective in order to maintain the above structural relationship. This slightly longer length is illustrated in FIGS. 1 and 2.

THE METHOD

As will be appreciated from reference to FIG. 1, the method of operation of the invention is integrally related to the apparatus 10 of the invention. The first step taken is to place the coated work piece 22 coated side up on the non-contaminating surface 20. The next step taken is to adjust the focusing knobs 24 in conjunction with the X-Y stage control 28 to obtain a clear focus through the eye pieces 16 in conjunction with the visual objective 14 to obtain a clear optical focus on the desired portion of the coated work piece 22. Once in focus, the distance from the surface of the coated work piece 22 to that of the surface of the objective 14 should be approximately 2-3 millimeters (the working distance of the objective 14).

The turret assembly 12 is then rotated to place the desired measuring thickness detector over the coated work piece 22. Typically, the measuring thickness (promethium 147) detector 30 would be rotated into place over the coated work piece 22 if the composition of the coated work piece 22 was, for example, CdTe on sapphire. In a similar fashion the measuring thickness detector 34 containing the strontium 90 isotope would be rotated into place over the coated work piece 22 if the coated work piece 22 were composed of HgCdTe on sapphire. Once the desired measuring thickness detector is in place over the coated work piece 22, the thickness measurement is taken. This is generally initiated via start button 42 on electronic readout counter unit 38. The final step is to remove the coated work piece 22 from the non-contaminating surface 20.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described what is claimed is:

1. A coating thickness measuring apparatus for measuring thickness of coatings on a work piece, comprising in combination:
   a base;
   a positioning means on said base for receiving and positioning a coated work piece thereon;
   a measuring detector provided with a radiation source and a radiation detector to determine said thickness of coatings on a work piece;
   a casing for housing said measuring detector, said casing having a body length and an aperture therein through which radiation can pass to strike a coated work piece;
   an optical focusing means for maintaning a repeatable, non-contacting operable distance between said casing and a coated work piece;
   a supporting means carried by said base and capable of supporting said casing and said focusing means;
   a means for displaying said thickness of a coated work piece.

2. The apparatus as set forth in claim 1, wherein said positioning means comprises:
   a non-contaminating surface upon which a coated work piece rests, and a means for controlling the X-Y movement of said non-contaminating surface, wherein said means for controlling the X-Y movement comprises a microscope stage and associated adjustment 3. The apparatus as set forth in claim 1, wherein said radiation detector is a beta-ray backscatter type of thickness measuring instrument comprising a Geiger-Mueller tube.

4. The apparatus as set forth in claim 1, wherein said optical focusing means comprises a microscope, having at least one objective having a body length and a working distance, and at least one eye piece.

5. The apparatus as set forth in claim 4, wherein said repeatable, non-contacting operable distance is maintained by the following structural relationship: said non-contacting operable distance=(said body length of said objective−said body length of said casing) +said working distance of said objective.

6. The apparatus as set forth in claim 1, wherein said supporting means further comprises a rotatable assembly.

7. The apparatus as set forth in claim 6, wherein said rotatable assembly comprises a microscope turret having at least one microscope visual objective and at least one said measuring detector attached thereto.

8. The apparatus as set forth in claim 1, wherein said supporting means further comprises a slidable assembly, said slidable assembly comprising at least one microscope objective and at least one said measuring detector attached thereto.

9. The apparatus as set forth in claim 1, wherein said casing further comprises:
   an upper and a lower portion, said upper portion having an exit orifice therein for input/output cables;
   an isotope pedestal positioned in said lower portion for holding said radiation source;
   an isotope set screw for attaching said isotope pedestal in said lower portion;
   a detector set screw for attaching said measuring detector into said lower portion;
   a means for connecting said upper and lower portions together;
   a means for connecting said upper portion to said supporting means.

10. A coating thickness measuring device, for contactless measuring of the thickness of coatings on a work piece, comprising in combination:
    a housing;
    a casing having a body length attached to said housing;
    a thickness measuring detector enclosed in said casing;
    an optical positioning means for locating said casing in a contactless position with respect to a coated work piece.

11. The thickness measuring device as set forth in claim 10, wherein said measuring detector is a beta-ray backscatter type of thickness measuring instrument comprising a Geiger-Mueller tube and a radioactive isotope, said Geiger-Mueller tube being connected via an input/output cable to a conventional electronic readout unit.

12. The thickness measuring device as set forth in claim 10, wherein said casing comprises:
    an upper and a lower portion, said upper portion having an exit orifice therein for input/output cables and said lower portion having an aperture therein through which radiation can pass to strike a coated work piece;

an isotope pedestal for holding a radiation source;

means for attaching said isotope pedestal in said lower portion of said casing;

a means for attaching said measuring detector in said lower portion of said casing;

a means for connecting said upper and lower portions of said casing together.

13. The thickness measuring device as set forth in claim 10, wherein said optical positioning means further comprises;

an optical focusing means for maintaining a repeatable, non-contacting operable distance between said casing and a coated work piece;

a supporting means carried by said housing and capable of supporting said casing and said focusing means.

14. The thickness measuring device as set forth in claim 13, wherein said optical focusing means comprises a microscope, having at least one visual objective having a body length and a working distance, and at least one eye piece.

15. The thickness measuring device as set forth in claim 14, wherein said repeatable, non-contacting operable distance is maintained by the following structural relationship: said non-contacting operable distance=(said body length of said visual objective−said body length of said casing)+said working distance of visual objective.

16. The thickness measuring device as set forth in claim 13, wherein said supporting means comprises a microscope turret having at least one microscope visual objective and at least one said measuring detector attached thereto.

17. A method of using an optical focusing system in conjunction with a radiation source and radiation detector for the non-destructive, contactless thickness measurement of contact sensitive coatings on work pieces, comprising the steps of:

(a) placing a coated work piece in a position to be measured;

(b) obtaining an optical focus on a portion of said coated work piece to be measured;

(c) positioning a beta-ray measuring instrument in a contactless position over said position of said work piece as located by said optical focus, such that the non-contacting operable distance is not greater than 5 millimeters;

(d) taking the thickness measurement of said work piece utilizing said beta-ray measuring instrument.

* * * * *